United States Patent
Diebold (10) Patent No.: US 8,644,929 B2
(45) Date of Patent: Feb. 4, 2014

(54) MEDICAL IMPLANT AND METHOD FOR SECURE IMPLANT COMMUNICATION

(75) Inventor: Michael Diebold, Berlin (DE)

(73) Assignee: Biotrnik SE & Co. KG (DE)

( * ) Notice: Subject to any disclaimer, the term of this patent is extended or adjusted under 35 U.S.C. 154(b) by 0 days.

(21) Appl. No.: 13/533,203

(22) Filed: Jun. 26, 2012

(65) Prior Publication Data

US 2013/0013016 A1    Jan. 10, 2013

Related U.S. Application Data

(60) Provisional application No. 61/504,707, filed on Jul. 6, 2011.

(51) Int. Cl.
*A61N 1/05* (2006.01)

(52) U.S. Cl.
USPC .......................................................... 607/18

(58) Field of Classification Search
USPC .......................................................... 607/18
See application file for complete search history.

(56) References Cited

U.S. PATENT DOCUMENTS

| 5,417,717 A * | 5/1995 | Salo et al. ........................ 607/18 |
| 2004/0147973 A1 | 7/2004 | Hauser |
| 2005/0203582 A1 | 9/2005 | Healy et al. |
| 2005/0283198 A1 | 12/2005 | Haubrich et al. |
| 2007/0282398 A1 | 12/2007 | Healy et al. |
| 2009/0281598 A1 | 11/2009 | Haubrich et al. |

OTHER PUBLICATIONS

European Search Report, No. 12172401.7-2305, Nov. 6, 2012, 3 pgs.

* cited by examiner

*Primary Examiner* — George Manuel
(74) *Attorney, Agent, or Firm* — Craig A. Fieschko, Esq.; DeWitt Ross & Stevens S.C.

(57) ABSTRACT

An implantable medical device includes a telemetry unit wirelessly receiving data signals and control commands; a control unit connected to the telemetry unit; and a comparator unit which compares data signals received via the telemetry unit with data signals generated in or detected by the implantable medical device. Each of the data signals represents specific features, e.g., patient characteristics. The comparator unit generates a release signal if data signals received via the telemetry unit represent one or more features that are similar, according to a specified similarity measure, to one or more features represented by data signals generated in or detected by the implantable medical device. The control unit executes control commands received via the telemetry unit, or receives control commands via the telemetry unit, in response to such a release signal (or, in the absence of the release signal, does not execute or receive control commands).

18 Claims, 4 Drawing Sheets

MEDICAL IMPLANT AND METHOD FOR SECURE IMPLANT COMMUNICATION

CROSS-REFERENCE TO RELATED APPLICATIONS

This application claims priority under 35 USC §119(e) to U.S. Provisional Patent Application 61/504,707 filed 6 Jul. 2011, the entirety of which is incorporated by reference herein.

FIELD OF THE INVENTION

The invention relates to an implantable medical device including a telemetry unit for wirelessly receiving data signals and control commands, and including a control unit connected to the telemetry unit.

BACKGROUND OF THE INVENTION

Implantable medical devices such as implantable cardiac pacemakers or implantable cardioverter/defibrillators often receive control commands via a telemetry unit, e.g., when an implant is remotely programmed via home monitoring. These control commands are typically intended to adapt and improve the operation of the implantable medical device, although they can impair operation if misuse occurs. Data communication between an external device and the implantable medical device should therefore be as secure as possible, and should preferably be authenticated. Since unauthorized personnel could reconfigure an active implantable medical device in ways that are potentially harmful to health, data access should be granted only to an authorized person or an authorized external device.

Currently, an inductive programming head is commonly used for data transmission to ensure patient security, and that authorized personnel are performing reconfiguration. The range of an inductive programming head is typically a few centimeters, and therefore the physician who is performing the reconfiguration must be located in the direct vicinity of the patient, which implicitly ensures authenticity.

It may be desirable to have a physician perform a reconfiguration remotely. In this instance, inductive telemetry should be replaced by radio frequency telemetry to avoid troubling the patient with the occasionally complicated placement of the programming head, which can be an error-prone endeavor for a layperson. Ranges of within a few meters are technically easy to attain, and therefore the patient's implant can be accessed without the need to be in his immediate vicinity. However, the use of radio frequency telemetry, with the greater range thereof, opens up new possibilities for compromising patient security. This has already been demonstrated in several publications.

It is therefore desirable to permit communication with the implant only when the external device reads a feature on the patient that may only be read directly and possibly only with the patient's permission, and that is compared by the implant with one of its own measurements for authentication. If they match, the implant can approve communication. A number of features might be extracted from the patient to perform an authentication:

Optical pulse measurement and comparison with an intracardial electrocardiogram (IEGM)
Measurement of the transit time of the radio signals and denial of access if the distance is too great
Application of an access code in the form of a tattooed barcode, number, or other indicia which is read by a camera Known solutions typically require additional hardware or do not solve the problem completely. A brief summary of the complexity of implementation is presented below:

Pulse Measurement

Implementation complexity is increased since an external device must be equipped with an optical pulse meter. This typically takes place on the finger. The solution is good in principle since a patient-specific feature is read, and the patient must actively "permit" the measurement.

Measurement of Transit Time

Implementation complexity is high since a special RF chip must be developed. Authentication is possible, although it is not possible for the patient to grant approval. In addition, the method is difficult for the patient to understand.

Tattooing

It is not particularly practical to apply features as tattoos. The security of authentication is good in principle, since authentication requires patient consent.

It would therefore be useful to have methods and devices that ensure maximum security and require only a reasonable amount of effort.

SUMMARY OF THE INVENTION

The foregoing issues can be addressed by an implantable medical device, as the active electrical implant, which includes a telemetry unit for wirelessly receiving data signals and control commands; a control unit connected to the telemetry unit; and a comparator unit configured to compare data signals received via the telemetry unit with data signals that are generated in, or detected by, the implantable medical device at the moment. The data signals represent specific feature sequences which can be compared with one another. The comparator unit is configured to generate a release signal if data signals received via the telemetry unit represent a feature, a combination of features, or a sequence of features that are similar, according to a specified similarity measure, to a feature, a combination of features, or a sequence of features represented by data signals generated in or detected by the implantable medical device at the moment. The control unit is configured to respond to such a release signal and execute control commands received via the telemetry unit, or to receive control commands via the telemetry unit and otherwise not execute or receive control commands.

The particular sequence of features represented by a data signal can be a sequence of physiological features that can be detected by the implant, or a sequence of signals generated by the implant itself. One example of a sequence of physiological features that can be detected by the implant is the sequence of cycle durations of consecutive cardiac cycles, which is transformed by the implant into a data signal that represents the individual cycles as a sequence of features.

The invention makes use of the finding that features that are known only to the communication partners should be used to ensure authenticity to establish secure data communication between the implant and the external device. In the case of the medical device presented here, these are features that are detected by or generated in the device itself at the moment, and that can therefore be read by an external device (or a combination of external devices) only with the patient's approval. Instead of a sequence of features, the data signals to be compared can also represent only a single feature that can be detected by or generated in the implant at the moment, or a combination of features that can be detected or generated simultaneously at the moment.

According to an alternative version in which the data signal detected by the implant at the moment represents a sequence of features derived from an intracardiac electrocardiogram, an external device such as a smart phone is used to record a patient's heart sounds, extract specific features, and send these features to the implant for comparison. The implant compares these specific features with a recorded intracardiac electrocardiogram (IEGM) and, if conformance is sufficient, permits data communication or the execution of control commands.

In other variants of the invention, the external device—possibly in combination with another external device—can be configured to:
 a) measure the heart sounds
 b) measure an electrocardiogram (ECG), and/or
 c) measure special sub-threshold pulses of the implant In the case of variants a) and b) above, the implantable medical device can include a detection unit for detecting current cardiac rhythm signals and generating data signals detected by the implantable medical device at the moment. The detection unit is connected to the control unit, and the comparator unit of the control unit is configured to compare data signals received by the telemetry unit with current cardiac rhythm signals detected by the detection unit, and to generate a release signal if data signals received via the telemetry unit represent a cardiac rhythm that is similar, according to a specified similarity measure, to a current cardiac rhythm represented by current data signals. The control unit is configured to respond to the release signal and execute control commands received via the telemetry unit, or to receive control commands via the telemetry unit (or in the absence of the release signal, to not execute or receive control commands).

In these variant versions, the patient's heart sounds are measured over a period of a few seconds using the external device, for instance. On the basis thereof, patient-specific features such as RR interval, mean frequency, frequency variations, etc., are determined and provided with a time stamp.

In the implant, a circular buffer is filled continuously with an intracardially measured electrocardiogram, and is likewise provided with a time stamp. At the onset of communication, the external device and the implant compare their clocks and determine the difference. The external device corrects the time stamp of the measurement in accordance with the difference, thereby enabling features to be easily compared in the implant. If the features match, the implant grants access to configurations.

Variants a) and b) are largely identical, although heart sounds are not recorded in variant b), and an external electrocardiogram is recorded instead and is used to determine the patient-specific features.

In the case of variant c), the implantable medical device includes a pulse generator configured to generate sub-threshold current or voltage pulses that are dimensioned such that they do not stimulate muscle cells, wherein the pulse generator is furthermore configured to generate sub-threshold current or voltage pulses in a sequence representing a non-guessable sequence of features. The implantable medical device also preferably includes a feature sequence generator that is configured to generate a non-guessable sequence of features, and that is connected to the pulse generator, wherein the pulse generator is configured to generate sub-threshold current or voltage pulses that represent the non-guessable sequence of features.

The implant and the external device each include a transmitter which exchange data using sub-threshold pulses, e.g., brief voltage pulses below the stimulation threshold of cardiac cells. The implant generates a non-guessable sequence and transmits it to the external device. Only this external device is capable of receiving the sequence from the implant.

In every case, but preferably in the case of variant c), the telemetry unit of the implantable medical device can be configured to exchange data via sub-threshold current or voltage pulses with a corresponding telemetry interface of the external device.

In variants a) and b) in particular, it is preferable for data signals generated in or detected by the implantable medical device at the moment to contain time stamp signals that are assigned to individual features in a sequence of features represented by data signals generated in or detected by the implantable medical at the moment, and to indicate the instant at which a feature occurred or was detected according to a timer internal to the device. This simplifies the correctly-timed comparison of data signals generated or detected by the implantable medical device with the data signals transmitted by the external device to the implantable medical device, since the data signals to be compared can be synchronized using the time stamp.

The invention also encompasses an external device including a telemetry interface for wirelessly transmitting data signals and control commands, which includes a detection unit for detecting a patient-specific physiological sequence of features, or a sequence of features generated by an implantable medical device, and which is configured to transmit data signals that represent a sequence of features detected at the moment via the telemetry interface to an implantable medical device. When used with the aforementioned variants a) and b), the detection unit can be configured to detect a sequence of features that represents the patient's current cardiac rhythm. In particular, a detection unit implemented with the aforementioned variant a) might detect a patient's heart sounds as a sequence of features, and generate data signals accordingly. A detection unit implemented with the aforementioned variant b) might detect a patient's superficial electrocardiogram as a sequence of features, and generate data signals accordingly. When used with the aforementioned variant c), the detection unit could be configured to detect sub-threshold current or voltage pulses on a patient's body.

The invention may also include a method for initiating secure data communication with an implantable medical device. A preferred method includes the following steps:
 (1) Detect or generate a sequence of features, or a combination of features, in an implantable medical device;
 (2) Detect a sequence of features, or a combination of features, using an external device;
 (3) Transmit data signals, which represent a sequence of features detected by the external device, or a combination of features detected by the external device, to the implantable medical device;
 (4) Compare the sequence of features or combination of features detected or generated by the implantable medical device with the sequence of features, or combination of features, represented by the data signals transmitted to the implantable medical device by the external device; and
 (5) Permit or deny the further telemetric data exchange, or permit or deny the execution of control commands that were transmitted to the implantable medical device by the external device, depending on the result of the comparison.

A telemetric data exchange and/or execution of control commands is permitted when the comparison shows sufficient similarity between sequences of features or combinations of features represented by the compared data signals.

The invention additionally relates to a system including an implantable medical device of the type discussed above, and one or more external devices.

BRIEF DESCRIPTION OF THE DRAWINGS

The invention will now be explained in greater detail with reference to an exemplary version depicted in the accompanying figures, which show.

DETAILED DESCRIPTION OF EXEMPLARY VERSIONS OF THE INVENTION

Figure 1:
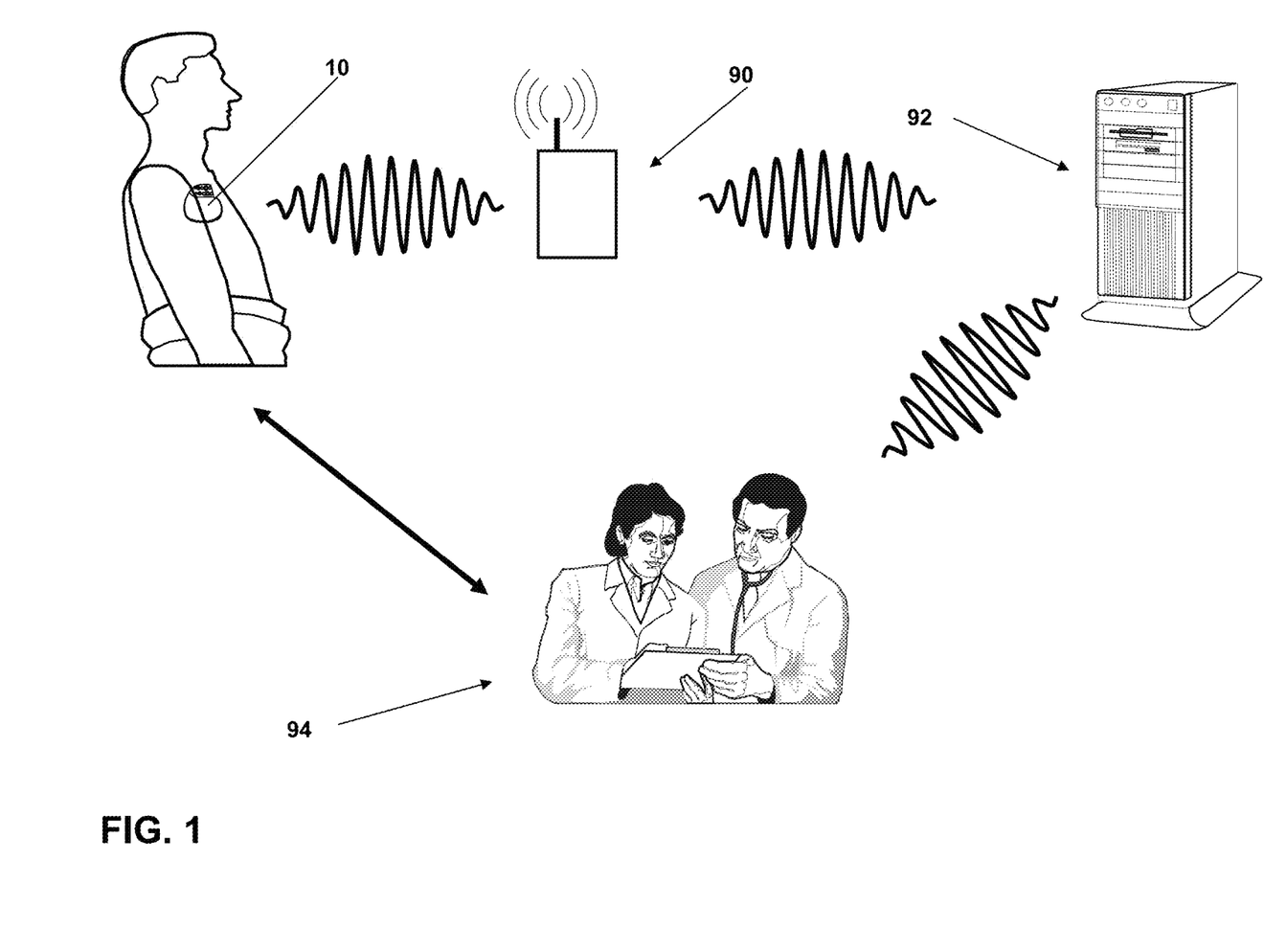
FIG. 1: a schematic depiction of a cardiac therapy system.

FIG. 1 shows an overview of a cardiac therapy system including an implantable cardiac pacemaker 10, an external device (patient device) 90, and a service center 110 represented symbolically by a server. The implantable cardiac stimulator 10 includes a telemetry unit 82 (see FIG. 3), via which it can exchange data wirelessly with the external device 90. The external device 90 is connected wirelessly to (for example) the service center 92, thereby enabling data to be exchanged between the service center 92 and the implantable cardiac stimulator 10 using the external device 90 as a relay station. A medical team 94 can access the service center 92 using data systems technology to view data that the service center 92 received from the implantable cardiac stimulator 10.

Figure 2:
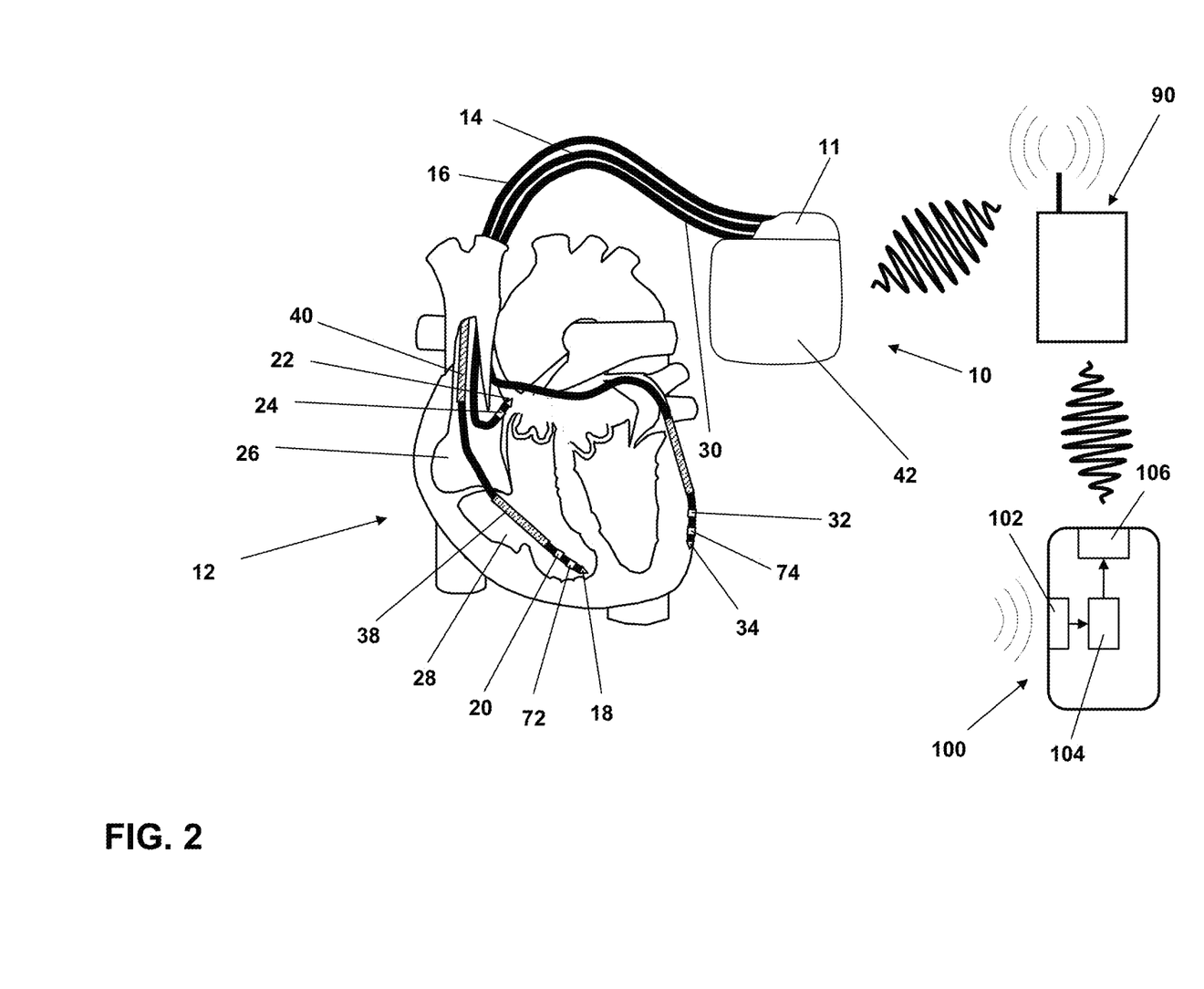
FIG. 2: a depiction of a cardiac stimulator with connected electrodes disposed in the heart.

FIG. 2 shows the implantable cardiac stimulator 10 in the form of a three-chamber cardiac pacemaker/cardioverter/defibrillator with electrode leads 14, 16 and 30 connected thereto and to a heart 12. An external device 90 disposed near the implantable cardiac stimulator 10 is also shown. The electrode leads 14, 16 and 30 are electrically connected using known, standardized plug connections to female contacts in a header (connection housing) 11 of the cardiac stimulator 10. In this manner, the electrode leads 14, 16 and 30 are also connected to electronic components in the interior of a hermetically sealed metal housing 42 of the cardiac stimulator 10. These components are presented schematically in greater detail in subsequent drawings, and determine the mode of operation of the cardiac stimulator 10.

The cardiac stimulator 10 is an implantable medical device and will therefore also be referred to in the following discussion as an implant.

The electrode lead 14 is a right-atrial electrode lead and includes on the distal end thereof an atrial tip electrode RA Tip 22 and, nearby, an atrial ring electrode RA Ring 24, both of which are located in the right atrium 26 of heart 12.

The electrode lead 16 is a right-ventricular electrode lead and includes on the distal end thereof a right-ventricular point electrode RV Tip 18 and, nearby, a right-ventricular ring electrode RA Ring 20. Both electrodes are located in the apex of the right ventricle 28 of heart 12. The right-ventricular electrode lead 16 also includes a large surface-area right-ventricular shock coil RV Shock 38 for delivering defibrillation shocks. Another shock coil 40 is disposed in the superior vena cava and is therefore also referred to below as the SVC shock electrode.

The electrode lead 30 is a left-ventricular electrode lead having a left-ventricular tip electrode LV Tip 34 on its distal end, and in the vicinity thereof, a left-ventricular ring electrode LV Ring 32. In addition, left-ventricular electrode lead 30 includes a left-ventricular shock coil, which is not described in greater detail but is depicted in FIG. 2, to deliver defibrillation shocks to the left ventricle. Left-ventricular electrode lead 30 is routed out of right atrium 26 of heart 12 via the coronary sinus into a lateral vein branching off therefrom, and is therefore also referred to as a coronary sinus electrode lead or CS electrode lead.

Figure 4:
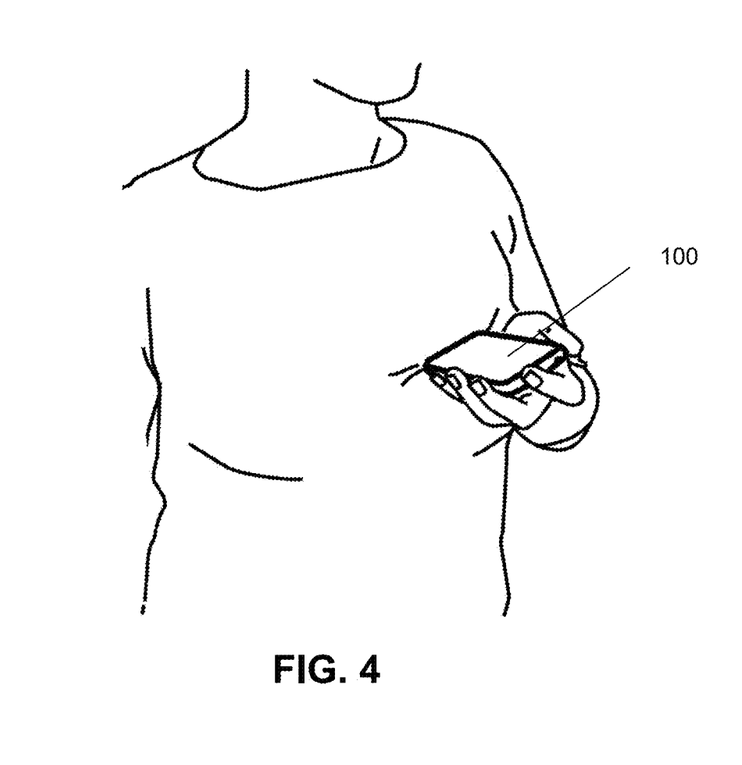
FIG. 4: a smart phone for listening to heart tones.
Figure 5:
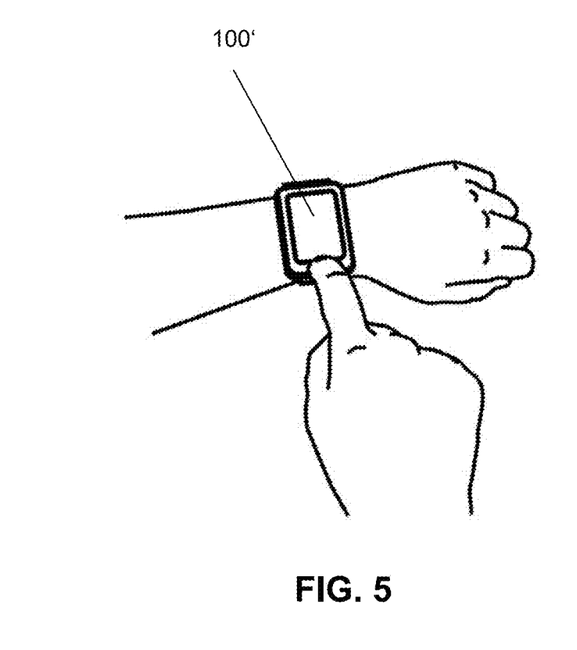
FIG. 5: a wristwatch with MICS telemetry or sub-threshold telemetry.

FIG. 2 also shows two external devices 90 and 100 wherein the external device 90 is configured to exchange data with the implantable cardiac stimulator 10. The external device 10 can also transmit control and programming commands to the telemetry unit 82 of the implantable cardiac stimulator 10 in this manner. The external device 100 is used to detect a current patient-specific sequence of features. To this end, the second external device 100 includes a detection unit 102 which contains (for example) a microphone configured to detect a patient's heart sounds, or electrodes which record a superficial electrocardiogram via a patient's skin, and/or electrodes which detect sub-threshold current or voltage pulses generated by the implantable cardiac stimulator 10. In a processing unit 104, the sequences of features detected by the external device 100 are processed further and supplied to a transmitter unit 106 which transmits a data signal that represents a particular sequence of features to the first external device 90. The first external device 90 is therefore capable of transmitting the data signal generated by the second external device 100 to the implantable cardiac stimulator 10, in order to authenticate itself. The second external device 100 can take the form of a common device such as a mobile telephone (e.g. a smart phone) or a type of wristwatch. Examples thereof are shown in FIGS. 4 and 5.

Instead of two external devices 90 and 100, the detection unit 102 can also be an integral component of the first external device 90. The mode of operation is then analogous to that described above, but the data connection between two external devices is made obsolete.

Figure 3:
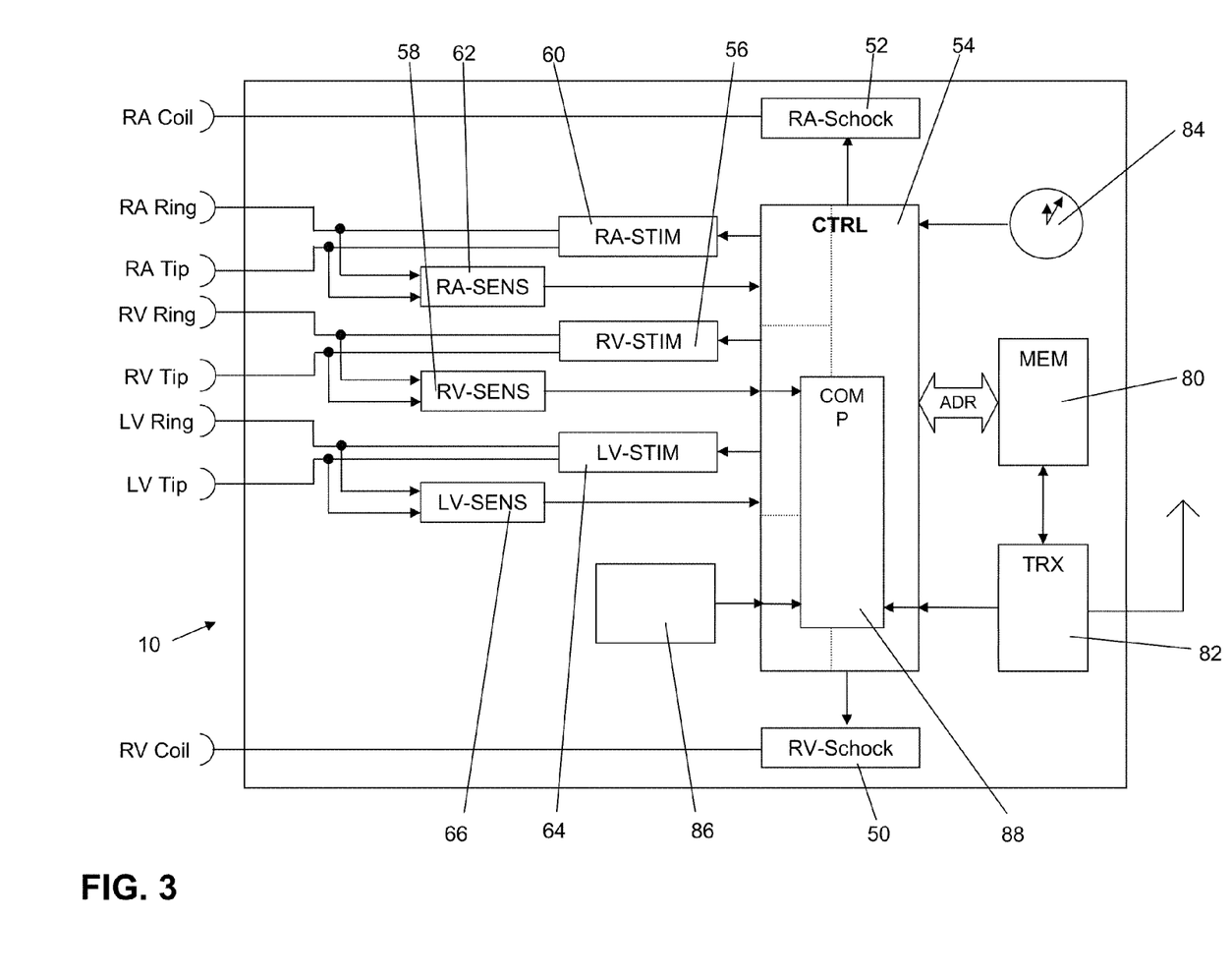
FIG. 3: a schematic block diagram of a cardiac stimulator.

The main components of the cardiac stimulator 10 are depicted in FIG. 3. The electrical connections for the various electrodes 18, 20, 22, 24, 32, 34, 38 and 40 are shown on the left side. Shock electrodes 38 and 40 are each connected to a right-ventricular shock pulse generator 50 or SVC shock generator 52. Shock generators 50 and 52 are connected to a control unit 54 which controls shock pulse generators 50 and 52 as needed to generate and deliver a defibrillation shock.

The connection for the right-ventricular tip electrode RV Tip and the connection for the right-ventricular ring electrode RV Ring are each connected to a right-ventricular stimulation unit 56 and a right-ventricular sensing unit 58. The right-ventricular stimulation unit 56 and the right-ventricular sensing unit 58 are both connected to the control unit 54.

The right-ventricular stimulation unit 56 is configured to generate a right-ventricular stimulation pulse in response to a trigger signal from the control unit 54 and deliver it in the connection for the right-ventricular ring electrode RV Ring and the right-ventricular tip electrode. As an alternative it is also possible for the housing 42 of the cardiac stimulator 10 to form a neutral electrode and for the right-ventricular stimulation unit 56 to be connected to the connection for the right-ventricular ring electrode RV Tip and the housing 42 as another electrode for delivering a stimulation pulse. A right-ventricular stimulation pulse differs from a defibrillation shock in that the pulse intensity of the stimulation pulse is substantially lower, and thus unlike a defibrillation shock, it does not stimulate all of the cardiac tissue (myocardium) of a ventricle at once, but only the cardiac muscle cells in the immediate vicinity of the right-ventricular tip electrode RV Tip 18. This stimulation then propagates by natural conduction across the entire ventricle, thereby stimulating contraction of the ventricle.

The right-ventricular sensing unit 58 is configured to initially amplify and filter electrical potentials present at the connection for the right-ventricular ring electrode RV Ring and the right-ventricular tip electrode RV Tip using an input amplifier. Furthermore, the right-ventricular sensing unit is configured to evaluate the course of electrical signals present at the inputs thereof such that the right-ventricular sensing unit 58 automatically detects a natural (intrinsic), i.e., automatic, contraction of the right ventricle. This can take place, for example, by comparing the course of the signal present at the inputs of the right-ventricular sensing unit 58 with a threshold value. Typically, the greatest amplitude of the signal in the form of the so-called R peak is characteristic of a natural contraction of the right ventricle, which can be detected by comparison with a threshold value. In response, the right-ventricular sensing unit 58 outputs a corresponding output signal to the stimulation control unit 54, indicating a natural contraction of the right ventricle.

The control unit 54 generates a data signal on the basis of the output signals of the sensing unit 58, and forwards the signal to a comparator unit 88.

An R peak can also be detected by an external device, such as a superficial electrocardiogram. A particular sequence of R peaks represents a patient's cardiac rhythm and, as such, is a sequence of features that, in terms of the time-related properties thereof, such as the length of the intervals of consecutive cardiac cycles, are characteristic of an individual person at a specific point in time.

The signal output by the right-ventricular sensing unit 58, or signal sequences derived therefrom, therefore form a data signal that represents a sequence of features that is characteristic for a person at a defined time.

The same sequence of features can be detected by the external device, e.g. by recording a superficial electrocardiogram or by recording heart tones, and using these to generate a corresponding data signal and transmit it telemetrically to the implantable cardiac stimulator 10.

The comparator unit 88 is configured to compare a detected data signal derived from the output signal of the sensing unit 58 with a data signal received via a telemetry unit 82.

The connection for the right-atrial tip electrode and the connection for the right-atrial ring electrode are connected to a right-atrial stimulation unit 60 and a right-atrial sensing unit 62 which, in turn, are connected to the control unit 54. The right-atrial stimulation unit 60 is configured to generate stimulation pulses having an intensity that is sufficient to stimulate the right-atrial myocardium. The right-atrial sensing unit 62 is configured to detect a so-called P wave on the basis of the course of the differential signal present at the inputs thereof; the P wave characterizes a natural (intrinsic) contraction of the right atrium. If right-atrial sensing unit 62 detects a corresponding P wave, it generates an output signal—which characterizes a natural contraction of the right atrium—and forwards it to the control unit 54. Such a P wave can also be detected by an external device, e.g., via a superficial electrocardiogram.

In the same manner, the connection for the left-ventricular tip electrode LV Tip and the connection for the left-ventricular ring electrode LV Ring are connected to a left-ventricular stimulation unit 64 and a left-ventricular sensing unit 66. The left-ventricular stimulation unit 64 and the left-ventricular sensing unit 66 are likewise connected to the control unit 54. Both of them function in a manner similar to that of the above-described is stimulation units 56 and 60 and the sensing units 58 and 62.

The cardiac stimulator 10 also includes a memory unit 80 which is connected to the control unit 54 and permits it to store signals that were generated or evaluated by the control unit 54, in particular data signals that represent an individual cardiac rhythm It also enables the memory unit 80 to store control programs or control commands, in changeable form, for the control unit 54.

Furthermore, the control unit 54 is connected to a timer 84 which enables the control unit 54, inter alia, to determine points in time and time intervals, and, in particular, to provide detected intrinsic events (i.e. detected P waves or R peaks, or both) with a time stamp, thereby ensuring that the data signals detected by the cardiac stimulator contain appropriate time stamps.

The memory unit 80 is connected to the telemetry unit 82, which enables data stored in memory unit 80 to be transmitted wirelessly to the external device 90, or enables the external device 90 to transmit programming or control commands to the cardiac stimulator 10 and store them in the memory unit 80. The telemetry unit 82 is configured to transmit data in the MICS (Medical Implant Communication Service) band, for instance. The MICS band is a frequency band between 402 and 405 MHz, which is intended specifically for data communication with medical implants. At the onset of transmission of control commands in particular, the cardiac stimulator receives a data signal via the telemetry unit 82 that the transmitting external device obtained from a sequence of features recorded on a patient's body. The data signal that is received likewise includes a time stamp for the events represented by the data signal.

This enables the control unit 54 and the comparator unit 88 of the cardiac stimulator 10 to compare a data signal it detected with a data signal received by an external device. If the comparison reveals that the data signal that was received represents a sequence of features that corresponds to the sequence of features represented by the detected data signal, within specified tolerances, the control unit 54 permits further data communication or enables the external device 90 to execute control commands that were received. Alternatively, if there is no correspondence, or correspondence outside the specified tolerances, further data communication and/or the execution of control commands may be prohibited.

In the version described so far, the patient's heart generates a non-guessable sequence of features that is detected by the cardiac stimulator 10 and the external device 100, and can be transformed into a data signal.

Alternatively, the cardiac stimulator 10 can also include a feature sequence generator 86 which is configured to generate a non-guessable sequence of features. The feature sequence generator 86 is connected, directly or indirectly, to at least one of the stimulation units 56, 60 or 64, e.g. via control unit 54, and triggers the stimulation units to generate sub-threshold current or voltage pulses in a sequence that represents the non-guessable sequence of features. Such a sequence of sub-threshold current or voltage pulses can be detected on a patient's body by the external device 100, and can be transformed into a corresponding data signal.

The feature sequence generator 86 is also connected to the comparator unit 88, thereby enabling the comparator unit 88 to compare a current feature sequence generated by the feature sequence generator 86 to a feature sequence represented by a data signal received by the external device 90. If the comparison reveals that the received data signal represents a sequence of features that corresponds to the sequence of features generated by the feature sequence generator 86, within specified tolerances, the control unit 54 permits further data communication or enables the external device 90 to execute control commands that were received. Alternatively, if correspondence is insufficient, the control unit 54 prevents further data communication or the execution of control commands.

Regarding the version depicted in FIG. 3, it is sufficient for the comparator unit 88 to be connected only to the sensing unit 58 and the telemetry unit 82, or to the memory 80, or only to the feature sequence generator 86 and the telemetry unit 82 or the memory 80.

FIG. 4 shows a second external device 100 in the form of a smart phone for listening to heart sounds, which is capable of transmitting a signal that represents the monitored heart sounds to the external device 90 or, alternatively, directly to the cardiac stimulator 10, via Bluetooth Low Energy. In the case of transmissions to the cardiac stimulator 10, Bluetooth Low Energy or a comparable RF or AF communication technology that is available in the smart phone can be used as the communication technology between the cardiac stimulator 10 and the smart phone.

To initiate secure data communication with the cardiac stimulator 10, a patient holds the external device 100, with the microphone (or other sensor) 102, against his chest in order to record a series of heart sounds (or other signals). At the same time, the electrical signals of the heart are recorded in the circular buffer as part of memory 80 of implant 10. Both of the recordings are provided with a time stamp. At the onset of the communication sequence, the implant 10 and the external device 90 or 100 determine the difference between their internal clocks in order to ensure that the two recordings are correlated in terms of time.

The external device 100 extracts from the heart sounds the time difference between consecutive heartbeats, with this time difference being specific to the patient. This information is transmitted to the implant 10, where it is compared with the features obtained from stored intracardial electrocardiograms. If the comparator unit 88 of the implant 10 identifies a correlation, it permits access to the configuration.

FIG. 5 shows a second external device 100' in the form of a wristwatch with MICS telemetry or sub-threshold telemetry. In a first sub-variant b) of this variant version, a wristwatch with MICS telemetry is used. By touching the backstay, the patient initiates a recording of the EKG measured between the two hands. Storage with time stamp and feature extraction also takes place.

In a second sub-variant c), a wristwatch with sub-threshold telemetry is used. In that case, the patient touches the backstay of a wristwatch which is equipped with sub-threshold telemetry technology and is designed as an electrode. The second electrode is formed by the housing base on the underside of the watch. The implant 10 generates a non-guessable sequence, which is derived (for example) by digitizing a noisy signal, in order to ensure maximum randomness, and transmits the sequence to the external device. Only this external device is capable of receiving the sequence of the implant via the backstay and housing base.

The various variants provide the following advantages. Initially, the aforementioned variant a) allows usage of smart phones, which are widely available on the market today, as the external device. The invention can therefore be implemented in software for various smart phone platforms which use the same RF or other telemetry (e.g., Bluetooth Low Energy) used by future implants. In terms of cost, the solution is therefore no longer dependent on the number of users.

The aforementioned variant b), using an EKG-measuring wristwatch, has the advantage absolutely certain authentication of access can be enabled using a simple approach, with the patient providing consent. Additionally, the known MICS telemetry can still be used.

The aforementioned variant c), using a wristwatch with sub-threshold telemetry, has the advantage that feature comparison is particularly easy to perform since the implant calculates an unambiguous sequence of signals that is used only once, and outputs the signals as a sub-threshold pulse. In addition, current consumption is particularly low with this type of data transmission.

It will be apparent to those skilled in the art that numerous modifications and variations of the described examples and versions are possible in light of the foregoing discussion. The disclosed examples and versions are presented for purposes of illustration only. Other alternate versions may include some or all of the features disclosed herein. Therefore, it is the intent to cover all such modifications and alternate versions that fall literally within the scope of the claims below, or which are equivalent to the claimed versions, or which otherwise come within the true scope of this invention.

What is claimed is:

1. An implantable medical device including:
   a. a telemetry unit configured to wirelessly receive data signals and control commands, and
   b. a control unit:
      (1) connected to the telemetry unit, and
      (2) including a comparator unit configured to:
         (a) compare data signals received via the telemetry unit over a period with data signals generated in or detected by the implantable medical device over the same period, and
         (b) generate a release signal if the data signals received via the telemetry unit over the period represent one or more features that are similar, according to a defined similarity measure, to one or more features represented by the data signals generated in or detected by the implantable medical device over the same period,
   wherein the control unit is configured to:
      i. execute control commands received via the telemetry unit in response to the release signal, and
      ii. not execute control commands received via the telemetry unit if no release signal is generated.

2. The implantable medical device of claim 1:
   a. further including a detection unit connected to the control unit, the detection unit being configured to:
      (1) detect current cardiac rhythm signals, and
      (2) generate current data signals therefrom,
   b. the control unit is configured to:
      (1) compare data signals received via the telemetry unit with the current data signals, and
      (2) generate a release signal if the data signals received via the telemetry unit represent a cardiac rhythm that is similar, according to a specified similarity measure, to the cardiac rhythm signals represented by the current data signals,
      (3) execute control commands received via the telemetry unit, and/or receive control commands via the telemetry unit, in response to the release signal.

3. The implantable medical device of claim 1 wherein the implantable medical device is an implantable cardiac stimulator.

4. The implantable medical device of claim 1 in combination with an external device including:
   a. a telemetry interface configured to wirelessly transmit data signals and control commands,
   b. a detection unit configured to:
      (1) detect a set of features over the period, wherein the set is patient-specific or is generated by an implantable medical device, and
      (2) transmit data signals that represent the set of features detected over the period via the telemetry interface to the implantable medical device.

5. The implantable medical device of claim 4 wherein the detection unit is configured to detect a set of features that represents a patient's cardiac rhythm over the period.

6. The implantable medical device of claim 5 wherein the detection unit is configured to detect a patient's superficial electrocardiogram as the set of features.

7. An implantable medical device including:
   a. a telemetry unit configured to wirelessly receive data signals and control commands;
   b. a pulse generator configured to generate sub-threshold electrical pulses:
      (1) dimensioned such that they do not stimulate muscle cells, and
      (2) in a sequence that represents a non-guessable sequence of features;
   c. a control unit:
      (1) connected to the telemetry unit, and
      (2) including a comparator unit configured to:
         (a) compare data signals received via the telemetry unit over a period with data signals generated in or detected by the implantable medical device over the same period, and
         (b) generate a release signal if the data signals received via the telemetry unit over the period represent one or more features that are similar, according to a defined similarity measure, to one or more features represented by the data signals generated in or detected by the implantable medical device over the same period;
      wherein the control unit is configured to:
         i. execute control commands received via the telemetry unit, and/or
         ii. receive control commands via the telemetry unit, in response to the release signal.

8. The implantable medical device of claim 7:
   a. further including a feature sequence generator:
      (1) connected to the pulse generator, and
      (2) configured to generate a non-gues sable set of features,
   b. wherein the pulse generator is configured to generate sub-threshold current or voltage pulses that represent the non-gues sable sequence of features.

9. An implantable medical device including:
   a. a telemetry unit configured to wirelessly receive data signals and control commands; and
   b. a control unit:
      (1) connected to the telemetry unit, and
      (2) including a comparator unit configured to:
         (a) compare data signals received via the telemetry unit over a period with data signals generated in or detected by the implantable medical device over the same period, and
         (b) generate a release signal if the data signals received via the telemetry unit over the period represent one or more features that are similar, according to a defined similarity measure, to one or more features represented by the data signals generated in or detected by the implantable medical device over the same period;
      wherein the control unit is configured to:
         i. execute control commands received via the telemetry unit, and/or
         ii. receive control commands via the telemetry unit, in response to the release signal;
      wherein the data signals generated in or detected by the implantable medical device over the same period contain time stamp signals:
         I. assigned to individual features in the one or more features represented by the data signals generated in or detected by the implantable medical device over the same period, and
         II. that indicate the instant at which a feature occurred or was detected according to a timer internal to the implantable medical device.

10. An implantable medical device in combination with an external device,
    a. the implantable medical device including:
       (1) a telemetry unit configured to wirelessly receive data signals and control commands; and
       (2) a control unit:
          (a) connected to the telemetry unit, and
          (b) including a comparator unit configured to:
             (i) compare data signals received via the telemetry unit over a period with data signals generated in or detected by the implantable medical device over the same period, and
             (ii) generate a release signal if the data signals received via the telemetry unit over the period represent one or more features that are similar, according to a defined similarity measure, to one or more features represented by the data signals generated in or detected by the implantable medical device over the same period; and
    c. the external device including:
       (1) a telemetry interface configured to wirelessly transmit data signals and control commands; and
       (2) a detection unit configured to:
          (a) detect a set of features over the period, wherein the set is patient-specific or is generated by an implantable medical device, and
          (b) transmit data signals that represent the set of features detected over the period via the telemetry interface to the implantable medical device:
    c. wherein:
       (1) the control unit is configured to:
          (a) execute control commands received via the telemetry unit, and/or
          (b) receive control commands via the telemetry unit, in response to the release signal;
       (2) the detection unit is configured to detect a set of features that represents a patient's cardiac rhythm over the period; and
       (3) the detection unit is configured to detect sounds of a patient's heart as the set of features.

11. An implantable medical device in combination with an external device,
    a. the implantable medical device including:
       (1) a telemetry unit configured to wirelessly receive data signals and control commands; and
       (2) a control unit:
          (a) connected to the telemetry unit, and
          (b) including a comparator unit configured to:

(i) compare data signals received via the telemetry unit over a period with data signals generated in or detected by the implantable medical device over the same period, and (ii) generate a release signal if the data signals received via the telemetry unit over the period represent one or more features that are similar, according to a defined similarity measure, to one or more features represented by the data signals generated in or detected by the implantable medical device over the same period; and c. the external device including:
(1) a telemetry interface configured to wirelessly transmit data signals and control commands; and
(2) a detection unit configured to:
(a) detect a set of features over the period, wherein the set is patient-specific or is generated by an implantable medical device, and
(b) transmit data signals that represent the set of features detected over the period via the telemetry interface to the implantable medical device:

c. wherein:
(1) the control unit is configured to:
(a) execute control commands received via the telemetry unit, and/or
(b) receive control commands via the telemetry unit, in response to the release signal; and
the detection unit is configured to detect sub-threshold current or voltage pulses on a patient's body as the set of features.

12. An implantable medical device in combination with an external device,
a. the implantable medical device including:
(1) a telemetry unit configured to wirelessly receive data signals and control commands; and
(2) a control unit:
(a) connected to the telemetry unit, and
(b) including a comparator unit configured to:
(i) compare data signals received via the telemetry unit over a period with data signals generated in or detected by the implantable medical device over the same period, and
(ii) generate a release signal if the data signals received via the telemetry unit over the period represent one or more features that are similar, according to a defined similarity measure, to one or more features represented by the data signals generated in or detected by the implantable medical device over the same period; and c. the external device including:
(1) a telemetry interface configured to wirelessly transmit data signals and control commands; and
(2) a detection unit configured to:
(a) detect a set of features over the period, wherein the set is patient-specific or is generated by an implantable medical device, and
(b) transmit data signals that represent the set of features detected over the period via the telemetry interface to the implantable medical device;

c. wherein:
(1) the control unit is configured to:
(a) execute control commands received via the telemetry unit, and/or
(b) receive control commands via the telemetry unit, in response to the release signal; and
(2) the telemetry unit of the implantable medical device and the telemetry interface of the external device are configured to perform data communication in the MICS frequency band.

13. The implantable medical device of claim 12 further including a second external device which includes a detection unit as recited in claim 4.

14. An implantable medical device in combination with an external device,
a. the implantable medical device including:
(1) a telemetry unit configured to wirelessly receive data signals and control commands; and
(2) a control unit:
(a) connected to the telemetry unit, and
(b) including a comparator unit configured to:
(i) compare data signals received via the telemetry unit over a period with data signals generated in or detected by the implantable medical device over the same period, and
(ii) generate a release signal if the data signals received via the telemetry unit over the period represent one or more features that are similar, according to a defined similarity measure, to one or more features represented by the data signals generated in or detected by the implantable medical device over the same period; and c. the external device including:
(1) a telemetry interface configured to wirelessly transmit data signals and control commands,
(2) a detection unit configured to:
(a) detect a set of features over the period, wherein the set is patient-specific or is generated by an implantable medical device, and
(b) transmit data signals that represent the set of features detected over the period via the telemetry interface to the implantable medical device;

c. wherein:
(1) the control unit is configured to:
(a) execute control commands received via the telemetry unit, and/or
(b) receive control commands via the telemetry unit, in response to the release signal; and
(2) the telemetry unit of the implantable medical device and the telemetry interface of the external device are configured to perform data communication using sub-threshold electrical pulses.

15. The implantable medical device of claim 14 further including a second external device which includes a detection unit as recited in claim 4.

16. An external device including:
a. a telemetry interface configured to wirelessly transmit data signals and control commands to an implantable medical device; and
b. a detection unit configured to:
(1) detect a set of features from a patient over a period, wherein the set is patient-specific or is generated by an implantable medical device; and
(2) transmit data signals that represent the set of features detected over the period via the telemetry interface to the implantable medical device;
wherein the detection unit is configured to detect:
i. a set of features that represents a patient's cardiac rhythm over the period; and
ii. sounds of a patient's heart as the set of features.

17. An external device including:
a. a telemetry interface configured to wirelessly transmit data signals and control commands to an implantable medical device; and
b. a detection unit configured to:
   (1) detect a set of features from a patient over a period, wherein the set is patient-specific or is generated by an implantable medical device; and
   (2) transmit data signals that represent the set of features detected over the period via the telemetry interface to the implantable medical device:
wherein:
i. the detection unit is configured to detect a set of features that represents a patient's cardiac rhythm over the period; and
ii. the detection unit is configured to detect a patient's superficial electrocardiogram as the set of features.

18. A method for initiating secure data communication between an implantable medical device and an external device, the method including the steps of:
a. obtaining a set of features using an implantable medical device, the set of features representing characteristics of a patient during a time period;
b. obtaining a set of features using an external device and generating data signals therefrom, the set of features representing characteristics of a patient over the same time period;
c. transmitting the data signals representing the set of features detected by the external device to the implantable medical device;
d. comparing the set of features obtained by the implantable medical device with the set of features represented by the data signals transmitted to the implantable medical device by the external device; and
e. only permitting the implantable medical device to execute control commands received from the external device if the data signals received by the implantable medical device represent one or more features that are similar, according to a defined similarity measure, to the set of features obtained by the implantable medical device.

* * * * *